United States Patent [19]
Amos et al.

[11] 3,982,895
[45] Sept. 28, 1976

[54] BLOOD SMEARED SLIDE CENTRIFUGE

[75] Inventors: Lynn G. Amos, Raleigh, N.C.;
James W. Bacus, Hinsdale, Ill.;
Robert C. Beaty; Charles H. Rogers, both of Raleigh, N.C.

[73] Assignee: Corning Glass Works, Corning, N.Y.

[22] Filed: June 18, 1974

[21] Appl. No.: 480,506

Related U.S. Application Data

[62] Division of Ser. No. 363,432, May 24, 1973, Pat. No. 3,906,890.

[52] U.S. Cl. .................................. 23/230 B; 233/26
[51] Int. Cl.² .................................. G01N 33/16
[58] Field of Search .............. 23/230 B; 356/39, 40, 356/102, 196, 197; 233/26; 117/3, 101; 424/3; 427/240

[56] References Cited
UNITED STATES PATENTS

| | | | |
|---|---|---|---|
| 3,402,883 | 9/1968 | Romer | 233/26 |
| 3,577,267 | 5/1971 | Preston, Jr. et al. | 117/101 |
| 3,705,048 | 12/1972 | Staunton | 117/3 |

*Primary Examiner*—Robert M. Reese
*Attorney, Agent, or Firm*—Walter S. Zebrowski; Clarence R. Patty, Jr.

[57] ABSTRACT

In the preparation of blood films for microscopic examination a slide spins in a centrifuge for a time which is a function of the red blood cell concentration of the blood. A drive circuit controls the time of spinning of a slide centrifuge. A variable control for the centrifuge motor includes a manual adjustment which is adjustable across a scale labeled as a function of the percent hematocrit of the blood.

4 Claims, 9 Drawing Figures

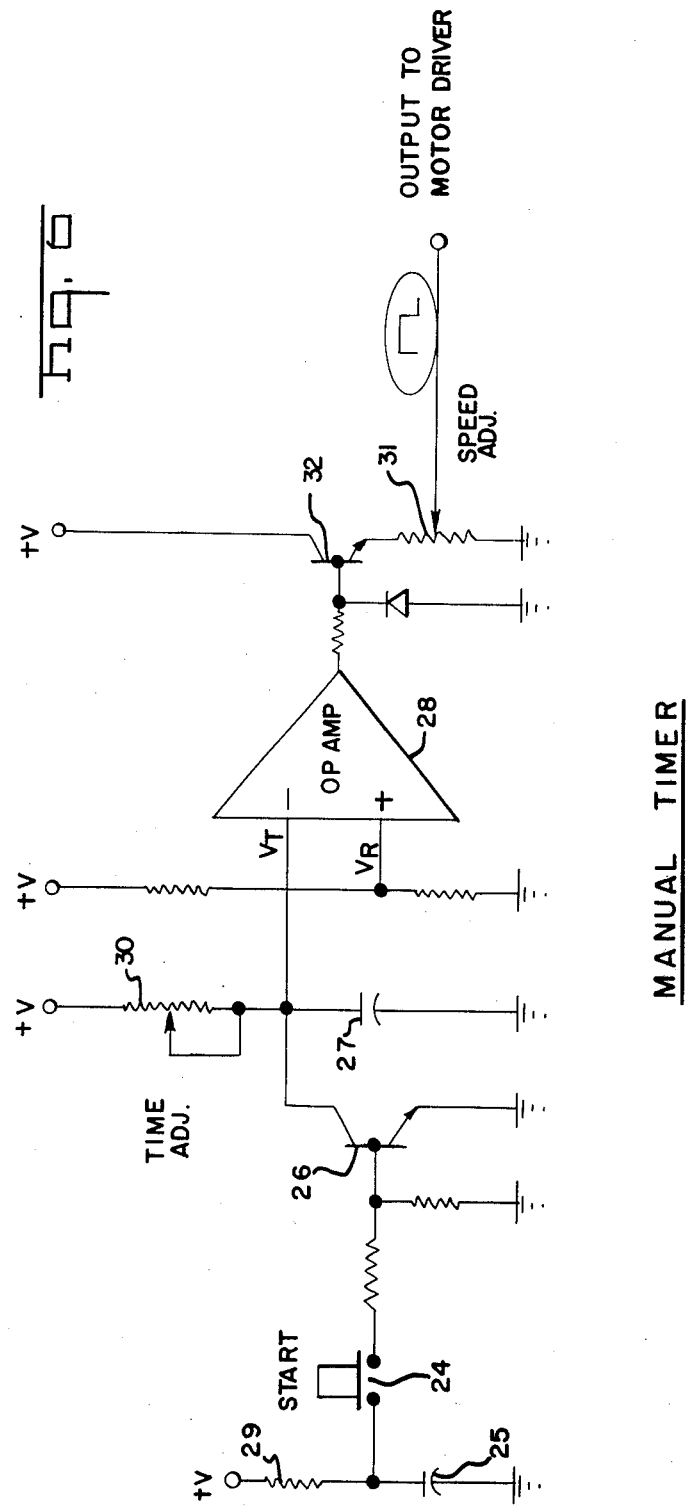

BLOOD SMEARED SLIDE CENTRIFUGE

This is a division of application Ser. No. 363,433, filed May 24, 1973, now U.S. Pat. No. 3,906,890.

BACKGROUND OF THE INVENTION

This invention relates to methods of, and apparatus for, preparing a blood smeared slide for analysis and more particularly to spinning the slide for a time which is a function of the red cell concentration of the blood.

In the analysis of blood samples, the blood is smeared on a laboratory slide and the smear is stained. By counting the leukocytes on the stained smear, laboratory technicians perform what is refered to as a white blood cell differential. Automation of this differential has significant enconomic impact because the differential is performed so frequently at every hospital. A thesis by J. W. Bacus, "An Automated Classification of the Peripheral Blood Leukocytes by Means of Digital Image Processing", University of Illinois, Chicago, 1971, describes one automated system.

Copending application Ser. No. 353,004 filed Apr. 20, 1973, by Douglas A. Cotter, "Image Scanning Converter for Automated Slide Analyzer", now U.S. Pat. No. 3,883,852, describes a system developed by my co-workers for automatically scanning and determining the relative number of different types of leukocytes on the stained smear.

Centrifugally spinning a blood wetted slide to produce a monolayer blood film is described in a paper by M. Ingram and F. M. Minter, "Semi-automatic Preparation of Coverglass Blood Smears Using a Centrifugal Device," Amer. J. Clin. Path. 51: 214–221, 1969. The method described in this paper includes flooding a coverglass with a layer of blood and centrifuging the coverglass rapidly in a plane parallel to the plane of rotation of the centrifuge. Excess blood is spun off leaving a monolayer of well spread blood cells on the cover glass.

Centrifuges for spinning blood smeared slides are commercially available. Such devices are available from: Plate General Corporation, (sold by PEI, Inc. 947 Old York Rd., Abington, Pennsylvania); Perkin-Elmer Corp., 50 Danbury Rd., Wilton, Conn.; and Shandon Scientific Co. Inc., 515 Broad St., Sewickley, Pennsylvania.

While some commercially available blood spinning apparatus have controls for adjusting the spin time, it has been the practice to set this spin time to one position and to allow it to remain there for all blood slide preparations.

After use of the centrifuges and blood spinning techniques described above, we have made the following observations.

The separation of the red cells was not the same for all blood samples. For some bloods the spinning resulted in blood films with sparsely populated areas interspersed with clumps of cells. For other bloods the technique produced a slide with overlapping cells.

As mentioned in the article by Ingram, the morphology of the red cells was often altered. The cells appeared overly flattened and noncircular. Often, white blood cells (specifically neutrophils appeared damaged.

For the blood film to be uniform, a large quantity of blood had to be used. Typically, the surface was flooded prior to spinning. If the entire surface was not wetted an irregular "sunburst" pattern of the blood resulted.

Manual methods for obtaining a blood smear (wedge and cover-slide method) require a skilled operator, are not very reproducible, and produce distributions which are non-uniform, often containing a high percentage of damaged cells.

U.S. Pat. Nos. 3,577,267 Preston et al. and 3,705,048 Staunton describe centrifuges which can be used to prepare blood slides but the apparatus described in these patents does not solve the problem of producing blood smears with good cell morphology and good cell distribution for all blood samples.

Accordingly, we have concluded that the preparation of a slide which is suitable for an automated white cell differential is a critical task which must be performed by a machine operated by an operator who need not make subjective judgments in order to get reproducible results.

SUMMARY OF THE INVENTION

In accordance with our invention blood films with good cell morphology and good cell distributions are produced by centrifuging the slide at a constant rotational velocity for a short period of time determined as a function of the red cell concentration.

In accordance with this invention apparatus for preparing a blood slide includes a centrifuge for spinning the slide and a drive circuit for controlling the time of spinning of the centrifuge. A variable control for the drive circuit is manually adjustable across a scale labeled as a function of the red blood cell concentration of the blood. In using this apparatus the operator observes the hematocrit (percent of blood volume occupied by red blood cells) either through tests or through observation. The operator sets the manual control to the indicated percent hematocrit of the blood. When the apparatus is started, the spin time is automatically adjusted in accordance with the blood hematocrit.

The foregoing and other objects, features and advantages of the invention will be better understood from the following more detailed description and appended claims.

DESCRIPTION OF THE DRAWINGS

FIG. 6 is a schematic diagram of the variable control; and

DESCRIPTION OF THE PREFERRED EMBODIMENT

Figure 1:
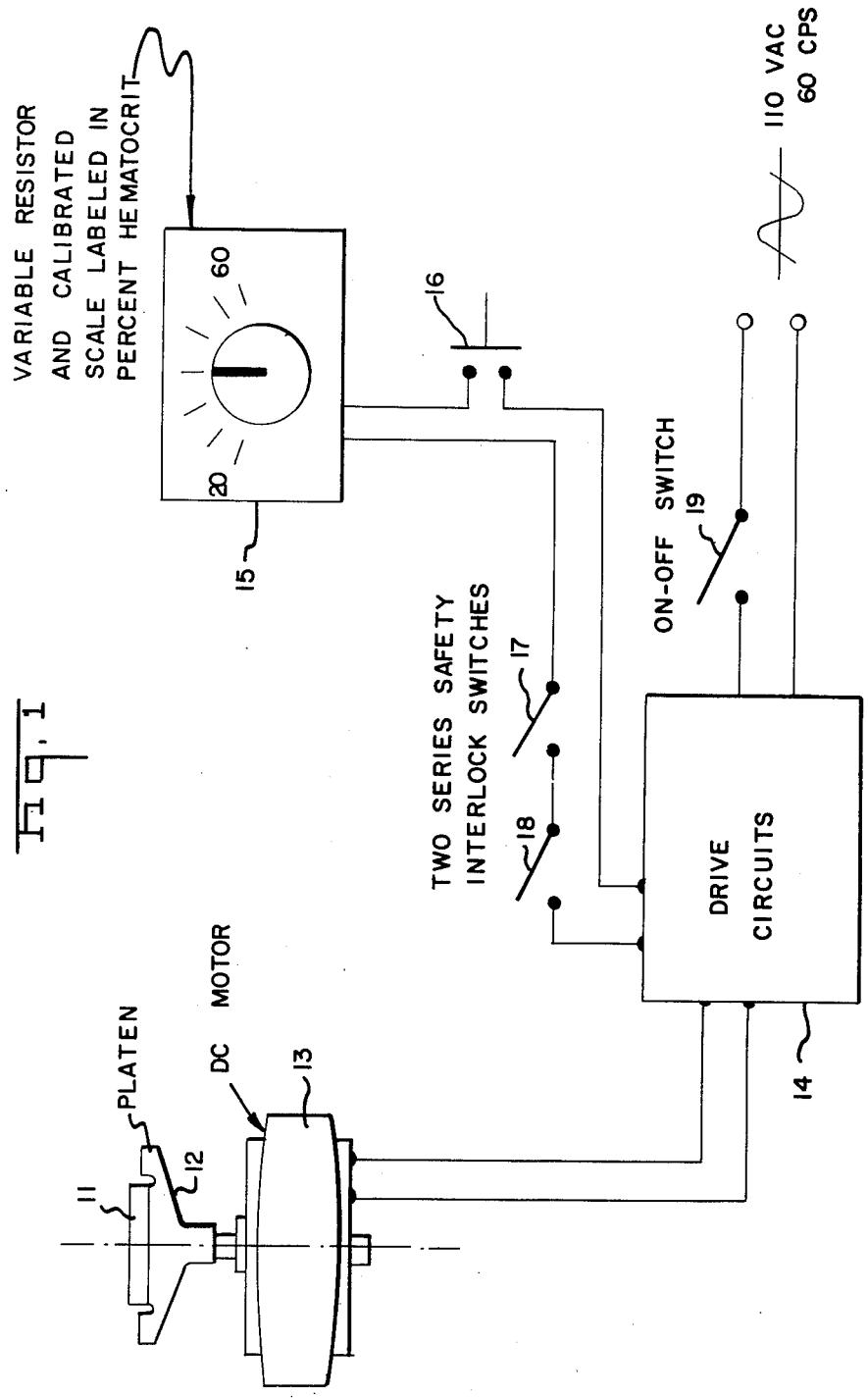
FIG. 1 is a schematic diagram of the blood spinning apparatus of this invention.
Figure 2:
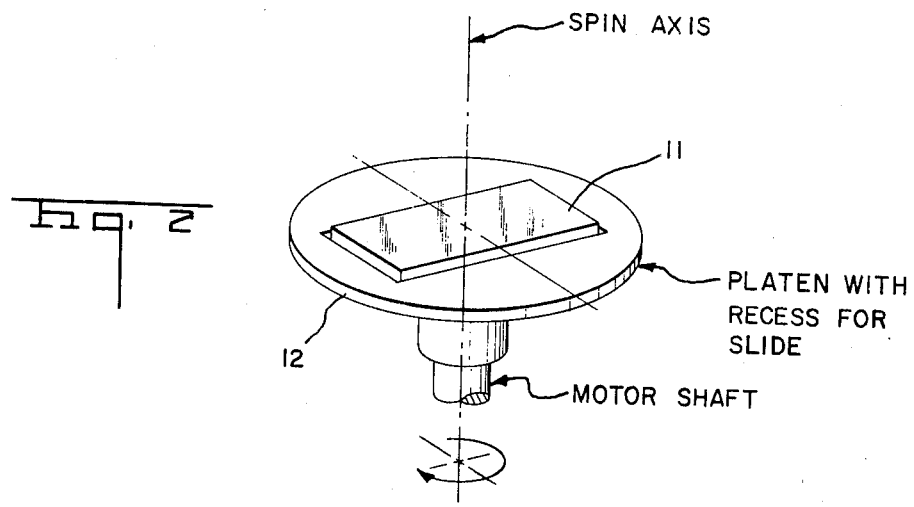
FIG. 2 shows the platen and a blood slide.

In FIGS. 1 and 2 the blood smeared slide 11 is positioned in a recess in a platen 12. The platen in fixed to the output shaft of a high torque, low inertia, DC motor 13.

A drive circuit 14 control the motor 13. A variable control 15 for the drive circuit includes a variable resistor which is adjusted in relationship to a scale labeled as a function of the red blood cell concentration of the blood. A start switch 16 starts the centrifuge motor which is rapidly accelerated to a selected rotational velocity. The motor is maintained at this selected velocity for a period of time determined by the variable control 15.

Two safety interlock switches 17 and 18 are actuated by a lid which covers the centrifuge. The centrifuge motor runs only when the lid is closed. This is a safety feature which prevents the slide from escaping the confines of the machine in the unlikely event of the slide slipping out of the recess in the platen.

An on-off switch 19 applies power to the drive circuit 14.

Figure 3:
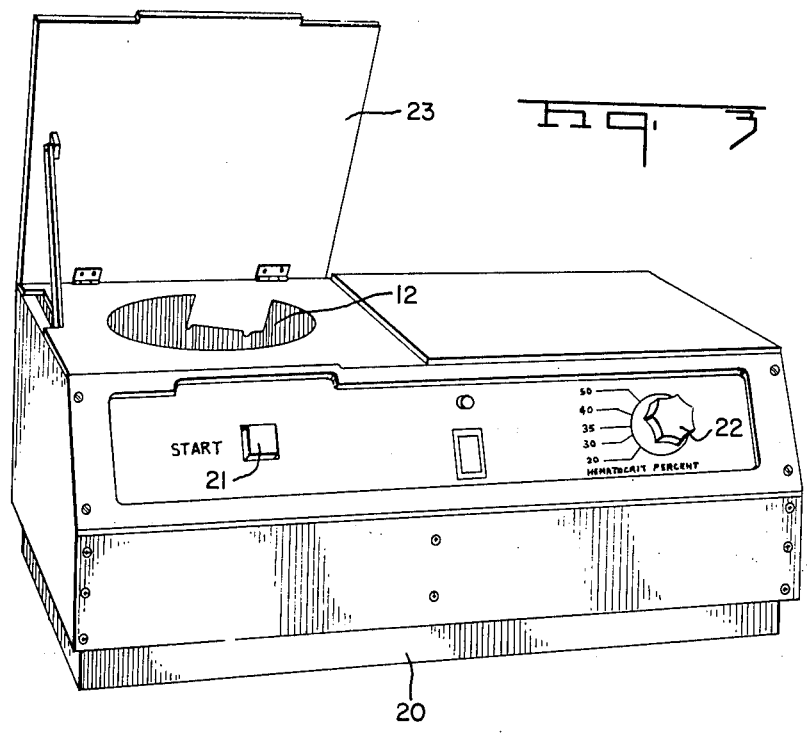
FIG. 3 is a pictorial view of the apparatus.

FIG. 3 depicts the housing 20 for the apparatus. It includes a hinged lid 23 which provides access to the platen. The hinged lid 23 actuates the safety interlock switches 17 and 18.

A start button 21 is provided to start the spin motor. The knob 22 adjusts the variable control in accordance with a scale labeled in hematocrit percent.

Figure 4:
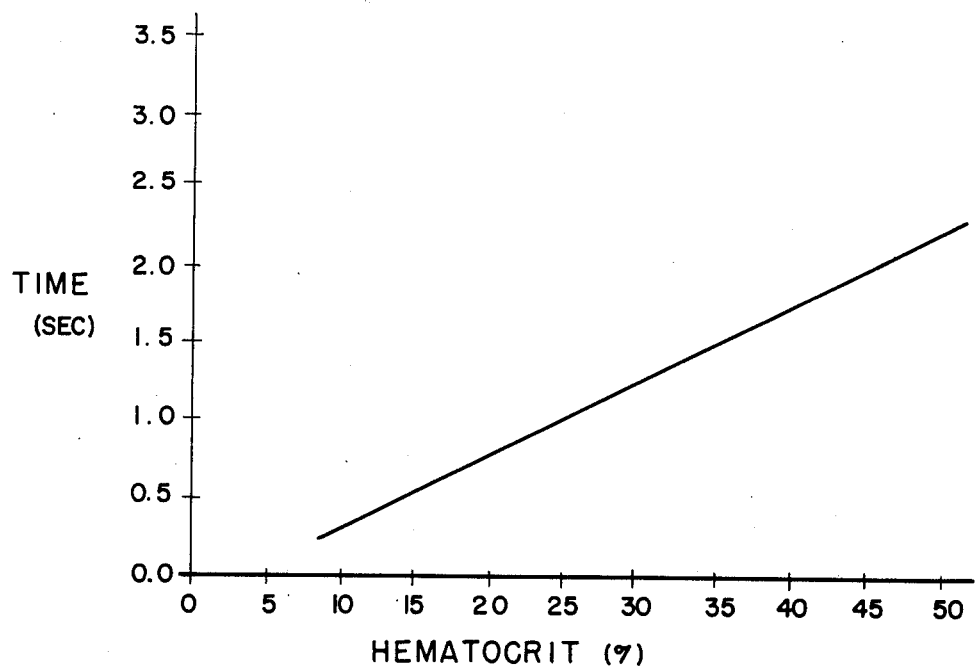
FIG. 4 shows hematocrit as a function of spin time.

FIG. 4 shows pin time as a function of blood hematocrit which we have found to be a good measure of the red blood cell concentration. Good films can be obtained by spinning slides at a constant velocity for a period of time which is a linear function of the hematocrit. Other measures of red blood cell concentration could be used. For example, hemoglobin concentration could be used as the measure. It is important that the centrifugal forces be applied to the blood longer, or in greater amounts, for increased red blood cell concentration. Therefore, the spin time can be held constant and the rotational speed can vary as a function of red blood cell concentration. Spin speed should be optimized to avoid altering the cell morphology. We have found that more damage to the cells occurs at high spin speeds than at lower spin speeds. By providing a rapid acceleration up to the final spin speed (requiring only 200–300 milliseconds) a motor speed of 5,000 R.P.M. can be used. At this speed the time can be adjusted as shown in FIG. 4 to obtain a good monolayer of blood.

Figure 5A:
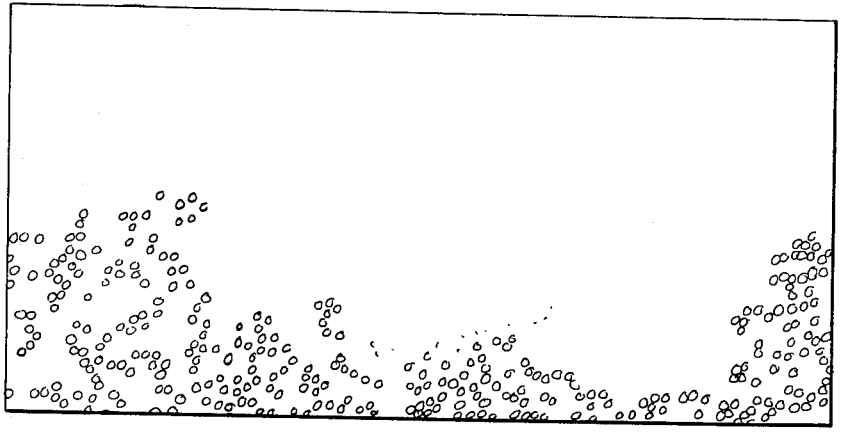
FIG. 5A depicts a blood side which has been centrifuged for too long a time.
Figure 5B:
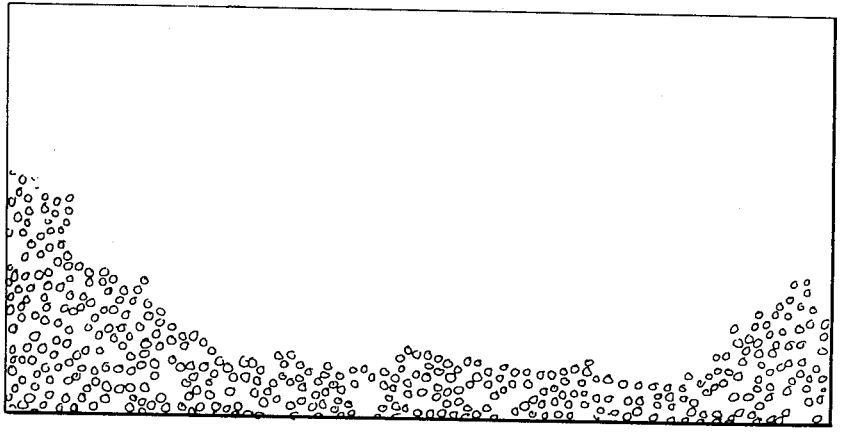
FIG. 5B depicts a blood slide which has been centrifuged for approximately the correct time.
Figure 5C:
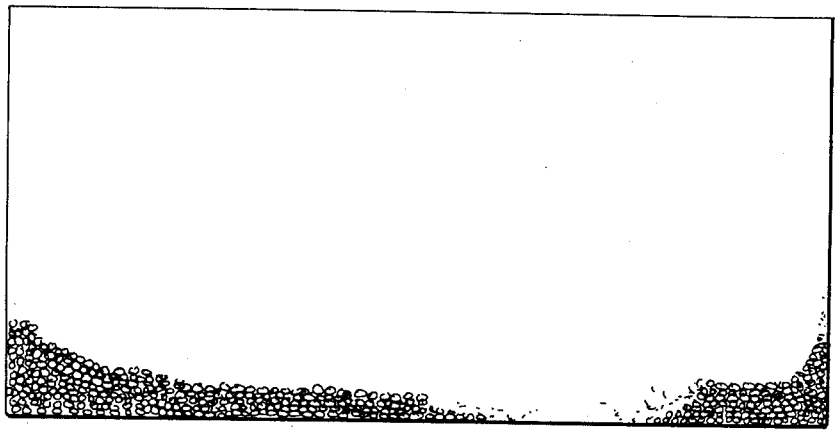
FIG. 5C depicts a blood slide which has not been centrifuged sufficiently long.

FIG. 5A depicts a microscope slide which has been centrifuged at too high a speed or for too long a time. The conventional red blood cell morphology has been destroyed, most cells being overly flattened or spread out. (In FIGS. 5A, B and C for convenience, only a portion of the slide has been depicted as blood smeared. Actually after centrifuging the entire slide should be uniformly coated.) FIG. 5B depicts a slide which has been correctly centrifuged. The conventional blood cell morphology is retained. In FIG. 5C the cell distribution is much too closely packed as a result of spinning for too short a time or at too low a speed.

Often, the operator has available an analysis of the blood giving the per cent of hematocrit in the blood. However, it is possible to estimate low, normal or high values of hematocrit based on the redness of the blood when exact percentages are not available.

FIG. 6 shows the variable control for adjusting the time of spinning. When the start button 24 is pushed the capacitor 25 is discharged. This turns the transistor 26 on This is turn discharges capacitor 27. Immediately the output of the operational amplifier 28 goes to the positive level. Because resistor 29 is large, the transistor 26 cannot remain on after the capacitor 25 has been discharged. Consequently, transistor 26 is turned off allowing capacitor 27 to be recharged through the variable resistor 30. Whe the voltage $V_T$ applied to the input of operational amplifier 28 returns to the level $V_R$, the output returns to a low level. This stops the motor. By varying the resistor 30 the time of the recharge and hence the time that the motor runs can be changed. The resistor 30 is disposed in relationship to a scale calibrated in per cent hematocrit of the blood.

Another variable resistor 31 changes the input voltage to the motor drive circuit thereby providing a speed control. The output to the motor driver circuit is provided by the transistor 32.

Figure 7:
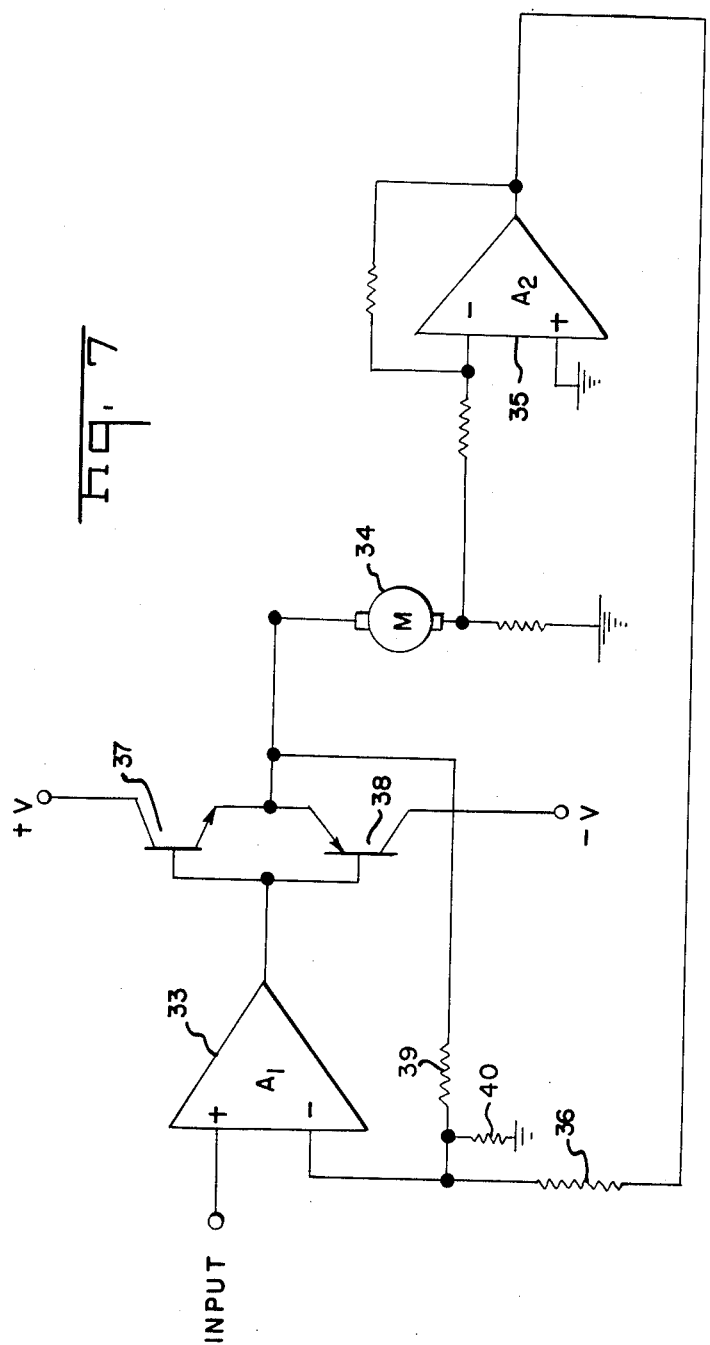
FIG. 7 is a schematic diagram of the drive circuit.

FIG. 7 shows the motor drive circuit. The input to this circuit comes from the control circuit of FIG. 6. The input is applied to the amplifier 33 whose output drives the DC motor 34.

Amplifier 35 develops a signal proportional to the negative of iR voltage drops in the motor. Resistors 36, 39 and 40 combine the output of amplifier 35 and the potential applied to the motor to yield a measure of back EMF which is directly proportional to motor speed. This feedback signal is then applied to the negative input of operational amplifier 33.

Transistors 37 and 38 provide the actual motor drive current. The operation is as follows. When the input from the drive circuit is positive, the motor 34 runs at a speed dependent on the voltage of the input signal. When the input voltage is zero the motor stops. Amplifier 33 compares the desired speed, at the positive input, with the actual speed as indicated by the back EMF signal applied to the negative input. The output of operational amplifier 33 is an error signal which turns the transistor 37 on to accelerate the motor or it turns transistor 38 on to de-accelerate the motor.

Summarizing, when the start button is pushed the input to the circuit of FIG. 7 goes positive. This turns on transistor 37 to provide a high voltage surge that brings the motor 34 up to a desired speed in a short period of time. The operational amplifier 35 and associated resistors sense the back EMF of the motor and develop a feedback signal proportional to actual motor speed. This is applied in a feedback loop which drives the motor at the regulated spin speed. When the input to the circuit of FIG. 7 returns to the zero level, the transistor 38 is turned on. This applied a reverse polarity current to the motor 34 to bring the motor to a stop in a short period of time.

While a particular embodiment of the invention has been shown and described various modifications are within the true spirit and scope of the invention. The appended claims are, therefore, intended to cover such modifications.

What is claimed is:

1. A method of preparing blood films for microscopic examination comprising
   determining the red blood cell concentration of a quantity of blood,
   placing a said quantity of blood on one flat surface of a microscope slide,
   providing a centrifuge,
   providing a manually-adjustable variable control,
   spinning said slide in said centrifuge with said one surface of said microscope slide perpendicular to the spin axis of said centrifuge, and
   controlling the time integral of the centrifugal force applied to said microscope slide by said centrifuge by adjusting with said variable control said time integral as a function of said red blood cell concentration of said blood.

2. The method recited in claim 1 wherein the blood hematocrit is used as a measure of red blood cell concentration.

3. The method recited in claim 1 wherein the speed of centrifuging is approximately 5,000 R.P.M. or less thereby reducing the number of damaged or ruptured blood cells.

4. The method recited in claim 3 wherein the spinning time as a function of hematocrit is that given in FIG. 4.

* * * * *